US00PP10690P

United States Patent [19]

Hanson

[11] Patent Number: Plant 10,690

[45] Date of Patent: Nov. 17, 1998

[54] HELIOPSIS PLANT NAMED 'LORAINE SUNSHINE'

[76] Inventor: Brent Jeffry Hanson, 502 N. Stevens St., Rhinelander, Wis. 54501

[21] Appl. No.: 910,472

[22] Filed: Jul. 25, 1997

[51] Int. Cl.[6] ..... A01H 5/00

[52] U.S. Cl. ..... Plt./68.1

[58] Field of Search ..... Plt./68.1

*Primary Examiner*—Howard J. Locker

*Assistant Examiner*—Kent L. Bell

*Attorney, Agent, or Firm*—C. A. Whealy

[57] ABSTRACT

A distinct cultivar of Heliopsis plant named 'Loraine Sunshine,' characterized by its unique green and white variegated foliage; relatively compact growth habit; freely branching plant habit; large golden yellow daisy-type inflorescences that flower throughout the summer; numerous inflorescences per plant; and good container and garden performance.

2 Drawing Sheets

The present invention relates to a new and distinct cultivar of Heliopsis plant, botanically known as *Heliopsis helianthoides scabra* and referred to by the cultivar name 'Loraine Sunshine'.

The new cultivar was selected in 1992 from seedling progeny from a cross of unidentified selections of *Heliopsis helianthoides scabra* in a cultivated outdoor area in Rhinelander, Wis.

Asexual reproduction of the new cultivar by terminal cuttings taken at Rhinelander, Wis., has shown that the unique features of this new Heliosis are stable and reproduced true to type in successive generations.

The following traits have been repeatedly observed and are determined to be the unique characteristics of 'Loraine Sunshine'. These characteristics in combination distinguish 'Loraine Sunshine' as a new and distinct cultivar:

1. Unique green and white variegated foliage.
2. Relatively compact growth habit.
3. Freely branching plant habit.
4. Large golden yellow daisy-type inflorescences that flower throughout the summer.
5. Numerous inflorescences per plant.
6. Good container and garden performance.

In contast to the new cultivar, plants of other known cultivars and selections of *Heliopsis helianthoides scabra* have solid green leaf color and are not compact.

The cultivar 'Loraine Sunshine' has not been observed under all possible environmental conditions. The phenotype may vary somewhat with variations in environment such as temperature, daylength and light intensity, without, however, any variance in genotype.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a top perspective view of a typical plant of the new Heliopsis.

The top photograph on the second sheet comprises a top perspective view of a typical plant of the new Heliosis in a garden setting.

The lower photograph on the second sheet comprises a close-up view of typical foliage and inflorescences of the new cultivar.

The floret and foliage colors in these photographs may vary from the actual floret and foliage colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Rhinelander, Wis.; Leola, Pa.; and Keller, Tex.

Botanical classification: *Heliopsis helianthoides scabra* cultivar 'Loraine Sunshine'.

Commercial classification: Garden or container Heliopsis.

Parentage: Seedling of unidentified *Heliosis helianthoides scabra* selections.

Propagation:

*Type.*—Vegetative stem and terminal tip cuttings.

*Time to rooting.*—Summer: 10 to 14 days at 21° C. soil temperature. Winter: About 14 days at 21° C. soil temperature.

*Rooting habit.*—Fine and well-branched.

Plant description:

*Appearance.*—Perennial herbaceous decorative container or garden plant. Stems upright, uniform rounded habit and freely branching. Removal of terminal apex (pinching) stimulates lateral branch development. Moderately vigorous and compact growth habit.

*Plant height.*—About 50 cm.

*Plant width.*—About 50 cm.

*Lateral branch description.*—Lateral branch diameter: About 3 mm. Internode length: About 5 cm. Texture: Pubescent, very fine and short hairs. Color: 144B with brownish red (close to 59A) overtones.

*Foliage description.*—Leaves variegated, veins green surrounded by white interveinal areas. Arrangement: Opposite, single. Length: About 9 cm. Width: About 4 cm. Shape: Ovate. Apex: Acute to cuspidate. Base: Cuneate to obtuse. Margin: Serrate. Texture: Short coarse hairs on upper surface gives a rough texture. Very fine, short hairs on lower surface. Petiole: Length: About 2.5 cm. Diameter: About 1 mm. Color: Young foliage upper surface: Veins: 139A. Interveinal areas: 155A. Young foliage under surface: Veins: Close to 139A, dulled. Interveinal areas: 155A. Fully expanded foliage upper surface: Veins: 139A. Interveinal areas: 155A. Fully expanded foliage under surface: Veins: 139A, dulled. Interveinal areas: 155A. Increased temperatures and light levels may cause variegation pattern to become less distinct. Petiole: 144A.

Flowering description:

*Appearance.*—Daisy inflorescence form. Inflorscences borne on terminals above foliage, arising from leaf axils. Disc and ray florets arranged acropetally on a capitulum. Usually one inflorescence per terminal, inflorescences upright and not persistent.

*Flowering response.*—Under natural conditions, plant flowers throughout the summer.

*Inflorescence size.*—Diameter: About 5.5 cm. Depth (height): About 1.5 cm. Diameter of disc: About 1.25 cm. Capitulum diameter: About 1.25 cm. Capitulum depth (height): About 8 mm.

*Ray florets.*—Quantity per inflorescence: About 13. Shape: Oblong, elongated. Length: About 3 cm. Width: About 1 cm. Apex: Dentate. Base: Attenuate, fused. Margin: Entire. Texture: Satiny, smooth and glabrous. Aspect: Flat. Color: When opening, upper surface: Brighter than 14A. When opening, under surface: 9A. Mature, upper surface: Brighter than 14A. Mature, under surface: 12A.

*Disc florets.*—Quantity per inflorescence: Numerous. Shape: Tubular. Length: About 8 mm. Width: About 1 mm. Color: Immature: 14A. Mature: 17A.

*Peduncle.*—Aspect: Flexible, strong and upright. Length: About 7.5 cm. Texture: Pubescent, very fine hairs. Color: 144A.

*Sepals.*—Arrangement: Fused at base. Quantity per inflorescence: About 15. Calyx length: About 7 mm. Calyx diameter: About 2 cm. Shape: Oblong. Apex: Acute. Margin: Entire, ciliate. Texture: Pubescent, very fine hairs. Color: Veins: 147A. Interveinal: 144A or lighter. Base: 144A.

*Inflorescence (bud).*—Length: About 1 cm. Diameter: About 1 cm. Shape: Cup-shaped. Color: 144A/147A.

*Reproductive organs.*—Androecium: Present on disc florets only. Stamen size: About 2 mm by 1 mm. Anther color: Brown at apex. Pollen: Abundant, yellow in color. Gynoecium: Present on both ray and disc florets. Pistil length: About 5 mm. Stigma shape: Two-parted. Stigma color: 17A.

Disease resistance: No known Heliopsis diseases observed to date on plants grown under commercial production conditions.

Seed production: Seed production has not been observed.

It is claimed:

1. A new and distinct cultivar of Heliopsis plant named 'Loraine Sunshine', as illustrated and described.

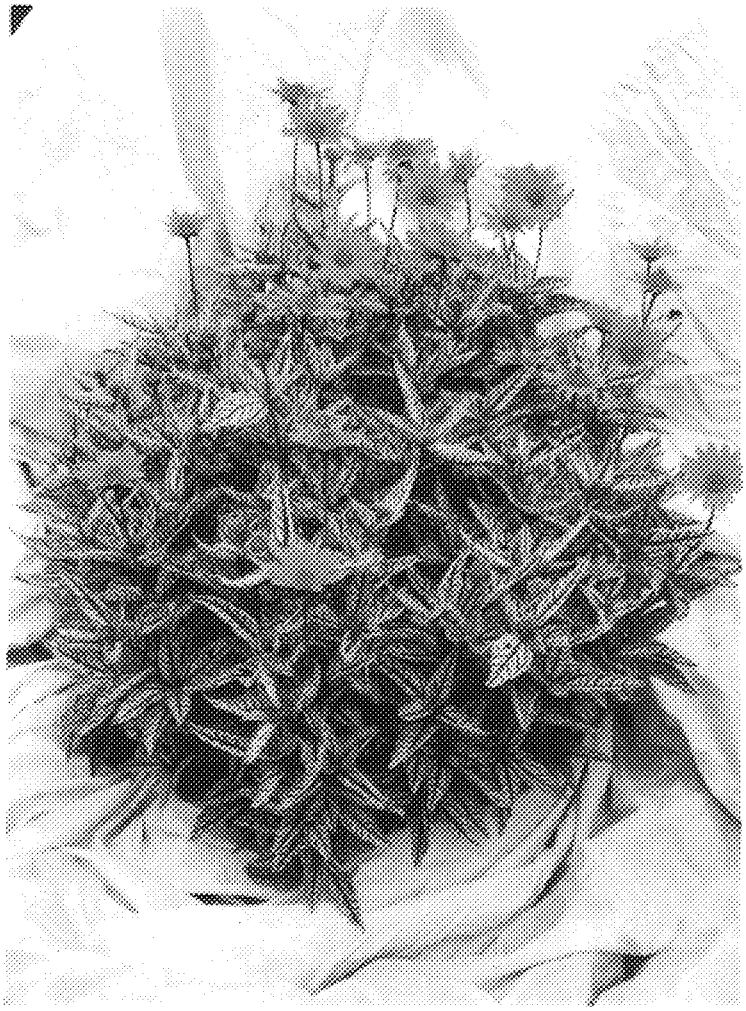

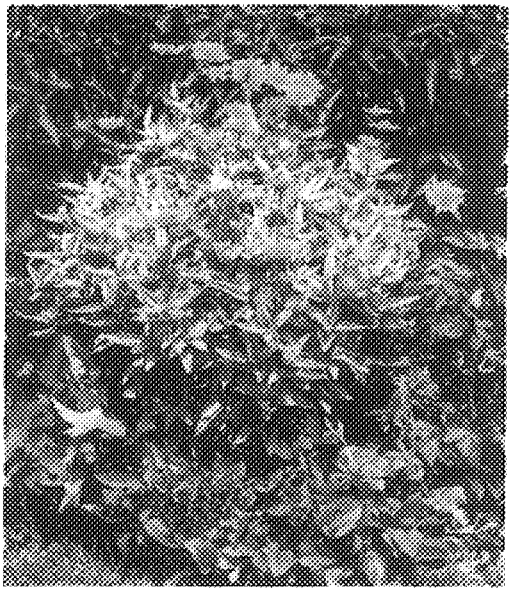
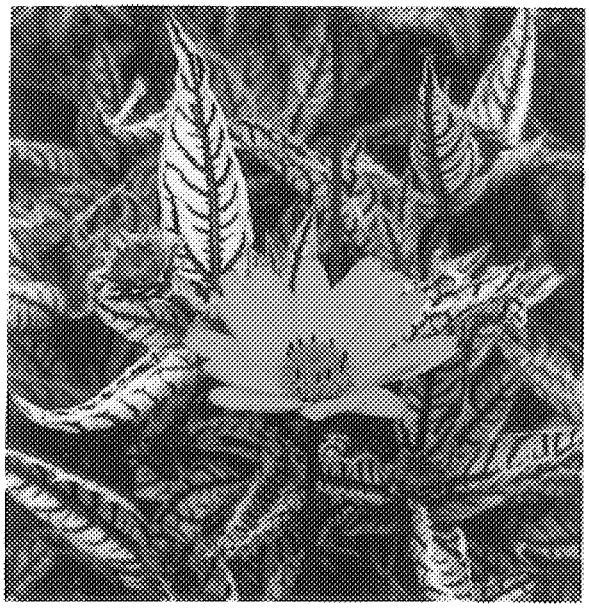

* * * * *